US010159963B2

(12) United States Patent
Loveless et al.

(10) Patent No.: US 10,159,963 B2
(45) Date of Patent: Dec. 25, 2018

(54) CATALYST FOR CONVERSION OF OXYGENATES TO AROMATICS

(71) Applicants: Brett Loveless, Maplewood, NJ (US); Rohit Vijay, Bridgewater, NJ (US); Samia Ilias, Somerville, NJ (US); Stephen J. McCarthy, Center Valley, PA (US)

(72) Inventors: Brett Loveless, Maplewood, NJ (US); Rohit Vijay, Bridgewater, NJ (US); Samia Ilias, Somerville, NJ (US); Stephen J. McCarthy, Center Valley, PA (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 350 days.

(21) Appl. No.: 14/560,099

(22) Filed: Dec. 4, 2014

(65) Prior Publication Data

US 2015/0174570 A1 Jun. 25, 2015

Related U.S. Application Data

(60) Provisional application No. 61/918,984, filed on Dec. 20, 2013, provisional application No. 61/918,994, filed on Dec. 20, 2013, provisional application No. 61/919,013, filed on Dec. 20, 2013.

(51) Int. Cl.

| | |
|---|---|
| *B01J 29/06* | (2006.01) |
| *B01J 29/40* | (2006.01) |
| *B01J 35/10* | (2006.01) |
| *B01J 29/70* | (2006.01) |
| *B01J 37/28* | (2006.01) |
| *B01J 23/06* | (2006.01) |
| *C07C 1/22* | (2006.01) |
| *B01J 27/14* | (2006.01) |
| *C07C 1/20* | (2006.01) |
| *C10G 3/00* | (2006.01) |
| *C10L 1/06* | (2006.01) |
| *B01J 38/02* | (2006.01) |
| *B01J 38/12* | (2006.01) |
| *B01J 21/04* | (2006.01) |
| *B01J 29/90* | (2006.01) |
| *B01J 37/02* | (2006.01) |
| *B01J 37/00* | (2006.01) |

(52) U.S. Cl.
CPC ............ *B01J 29/405* (2013.01); *B01J 21/04* (2013.01); *B01J 23/06* (2013.01); *B01J 27/14* (2013.01); *B01J 29/061* (2013.01); *B01J 29/40* (2013.01); *B01J 29/7049* (2013.01); *B01J 29/7057* (2013.01); *B01J 29/90* (2013.01); *B01J 35/10* (2013.01); *B01J 35/108* (2013.01); *B01J 35/109* (2013.01); *B01J 35/1014* (2013.01); *B01J 35/1019* (2013.01); *B01J 35/1023* (2013.01); *B01J 35/1038* (2013.01); *B01J 35/1042* (2013.01); *B01J 35/1057* (2013.01); *B01J 37/0201* (2013.01); *B01J 37/28* (2013.01); *B01J 38/02* (2013.01); *B01J 38/12* (2013.01); *C07C 1/20* (2013.01); *C07C 1/22* (2013.01); *C10G 3/45* (2013.01); *C10G 3/49* (2013.01); *C10G 3/55* (2013.01); *C10L 1/06* (2013.01); *B01J 37/0009* (2013.01); *B01J 2229/186* (2013.01); *B01J 2229/20* (2013.01); *B01J 2229/42* (2013.01); *C07C 2523/06* (2013.01); *C07C 2529/06* (2013.01); *C07C 2529/40* (2013.01); *C07C 2529/70* (2013.01); *C10L 2200/0423* (2013.01); *C10L 2200/0469* (2013.01); *C10L 2270/023* (2013.01); *Y02P 20/584* (2015.11); *Y02P 30/20* (2015.11); *Y02P 30/42* (2015.11)

(58) Field of Classification Search
CPC .................. C07C 2529/06; C07C 2529/40
USPC .......................... 502/60, 64, 65, 71, 73, 77
See application file for complete search history.

(56) References Cited

U.S. PATENT DOCUMENTS

| | | |
|---|---|---|
| 3,354,078 A | 11/1967 | Maile et al. |
| 3,702,886 A | 11/1972 | Argauer et al. |
| 3,709,979 A | 1/1973 | Chu |
| 3,760,024 A | 9/1973 | Cattanach |
| 3,832,449 A | 8/1974 | Rosinski et al. |
| 3,894,102 A | 7/1975 | Chang et al. |
| 3,894,103 A | 7/1975 | Chang et al. |
| 3,894,104 A | 7/1975 | Chang et al. |
| 3,894,107 A | 7/1975 | Butter et al. |

(Continued)

FOREIGN PATENT DOCUMENTS

| | | |
|---|---|---|
| CN | 101602643 | 12/2009 |
| CN | 101602648 | 12/2009 |

(Continued)

OTHER PUBLICATIONS

Huang et al., Machine translation of CN 101823929, Sep. 2010.*
International Search Report and Written Opinion from PCT/US2014/068612 dated Feb. 23, 2015.
International Search Report and Written Opinion from PCT/US2014/068625 dated Mar. 4, 2015.

(Continued)

*Primary Examiner* — Elizabeth D Wood
(74) *Attorney, Agent, or Firm* — Liza Negron (57) ABSTRACT

Catalyst compositions including a zeolite having a molar ratio of silicon to aluminum of about 10.0 to about 300.0; a Group 10-12 element and combinations thereof; a Group 15 element and combinations thereof; and optionally, a binder, wherein the catalyst composition has a molar ratio of Group 15 element to Group 10-12 element of about 0.01 to about 10.0 are disclosed. Methods of converting organic compounds to aromatics using such catalyst compositions are also disclosed.

17 Claims, 2 Drawing Sheets

(56) References Cited

U.S. PATENT DOCUMENTS

| | | | |
|---|---|---|---|
| 3,928,483 A | 12/1975 | Chang et al. | |
| 3,960,978 A | 6/1976 | Givens et al. | |
| 4,012,245 A | 4/1977 | Plank et al. | |
| 4,016,218 A | 4/1977 | Haag et al. | |
| 4,021,502 A | 5/1977 | Plank et al. | |
| 4,025,571 A | 5/1977 | Lago | |
| 4,035,430 A | 7/1977 | Dwyer et al. | |
| 4,046,685 A | 9/1977 | Bray | |
| 4,049,573 A | 9/1977 | Kaeding | |
| 4,058,576 A | 11/1977 | Chang et al. | |
| 4,076,842 A | 2/1978 | Plank et al. | |
| 4,079,095 A | 3/1978 | Givens et al. | |
| 4,088,706 A | 5/1978 | Kaeding | |
| 4,120,910 A * | 10/1978 | Chu | C07C 2/00 208/120.05 |
| RE29,948 E | 3/1979 | Dwyer et al. | |
| 4,150,062 A | 4/1979 | Garwood et al. | |
| 4,157,293 A | 6/1979 | Plank et al. | |
| 4,211,640 A | 7/1980 | Garwood et al. | |
| 4,227,992 A | 10/1980 | Garwood et al. | |
| 4,229,424 A * | 10/1980 | Kokotailo | B01J 29/40 423/325 |
| 4,288,645 A | 9/1981 | Wagstaff | |
| 4,291,182 A | 9/1981 | Dautzenberg et al. | |
| 4,326,994 A | 4/1982 | Haag et al. | |
| 4,397,827 A | 8/1983 | Chu | |
| 4,403,044 A | 9/1983 | Post et al. | |
| 4,417,780 A | 11/1983 | Knapp | |
| 4,423,274 A | 12/1983 | Daviuduk et al. | |
| 4,433,185 A | 2/1984 | Tabak | |
| 4,433,189 A | 2/1984 | Young | |
| 4,450,311 A | 5/1984 | Wright et al. | |
| 4,456,779 A | 6/1984 | Owen et al. | |
| 4,481,173 A * | 11/1984 | Chu | B01J 29/40 423/326 |
| 4,538,017 A | 8/1985 | Butler et al. | |
| 4,556,477 A | 12/1985 | Dwyer | |
| 4,579,993 A | 4/1986 | Bowes et al. | |
| 4,582,815 A | 4/1986 | Bowes | |
| 4,584,423 A | 4/1986 | Nacamuli et al. | |
| 4,590,321 A | 5/1986 | Chu | |
| 4,621,161 A | 11/1986 | Shihabi | |
| 4,628,135 A | 12/1986 | Owen et al. | |
| 4,665,251 A | 5/1987 | Chu | |
| 4,720,602 A | 1/1988 | Chu | |
| 4,788,369 A | 11/1988 | Marsh et al. | |
| 4,808,763 A | 2/1989 | Shum | |
| 5,110,572 A * | 5/1992 | Calabro | B01D 53/8628 423/705 |
| 5,365,004 A | 11/1994 | Beck et al. | |
| 5,367,099 A | 11/1994 | Beck et al. | |
| 5,625,103 A | 4/1997 | Abichandani et al. | |
| 5,633,417 A | 5/1997 | Beck et al. | |
| 5,675,047 A | 10/1997 | Beck et al. | |
| 5,705,726 A | 1/1998 | Abichandani et al. | |
| 5,877,368 A | 3/1999 | Kiyama et al. | |
| 5,883,034 A * | 3/1999 | Drake | B01J 23/06 502/208 |
| 5,898,089 A * | 4/1999 | Drake | B01J 23/06 208/134 |
| 5,932,777 A * | 8/1999 | Sughrue, II | C10G 61/00 208/135 |
| 5,998,688 A | 12/1999 | Abichandani et al. | |
| 6,028,238 A | 2/2000 | Beck et al. | |
| 6,048,815 A | 4/2000 | Yao et al. | |
| 6,083,865 A * | 7/2000 | Drake | B01J 23/06 502/60 |
| 6,156,689 A | 12/2000 | Kimble et al. | |
| 6,177,374 B1 | 1/2001 | Pradhan et al. | |
| 6,187,982 B1 | 2/2001 | Beck et al. | |
| 6,372,680 B1 | 4/2002 | Wu et al. | |
| 6,372,949 B1 | 4/2002 | Brown et al. | |
| 6,417,421 B1 * | 7/2002 | Yao | B01J 29/40 585/418 |
| 6,423,879 B1 | 7/2002 | Brown et al. | |
| 6,504,072 B1 | 1/2003 | Brown et al. | |
| 7,285,511 B2 | 10/2007 | Ghosh et al. | |
| 7,304,194 B2 | 12/2007 | Ghosh et al. | |
| 7,453,018 B2 | 11/2008 | Dakka et al. | |
| 7,722,825 B1 | 5/2010 | Bizzabi et al. | |
| 7,799,962 B2 | 9/2010 | Dakka et al. | |
| 2006/0161035 A1 | 7/2006 | Kalnes et al. | |
| 2007/0275852 A1 * | 11/2007 | Luo | B01J 29/46 502/213 |
| 2013/0060070 A1 * | 3/2013 | Huber | C10B 49/22 585/242 |
| 2013/0123557 A1 | 5/2013 | McCarthy et al. | |
| 2013/0158323 A1 * | 6/2013 | Mondal | B01J 29/40 585/408 |
| 2013/0165725 A1 * | 6/2013 | Chewter | C07C 1/20 585/450 |
| 2013/0281753 A1 | 10/2013 | McCarthy et al. | |
| 2013/0303814 A1 | 11/2013 | Mammadov et al. | |
| 2014/0018592 A1 | 1/2014 | Chen et al. | |
| 2016/0024392 A1 * | 1/2016 | Keusenkothen | C07C 1/0425 585/321 |
| 2016/0145496 A1 * | 5/2016 | Sorensen | C10B 53/02 201/2.5 |

FOREIGN PATENT DOCUMENTS

| | | |
|---|---|---|
| CN | 101607864 | 12/2009 |
| CN | 101780417 | 7/2010 |
| CN | 101823929 | 9/2010 |
| EP | 123449 A1 | 10/1984 |
| EP | 172686 A1 | 2/1986 |
| WO | 9951549 A1 | 10/1999 |
| WO | 129152 A1 | 4/2001 |
| WO | 2005068406 A1 | 7/2005 |
| WO | 2006012150 A2 | 2/2006 |
| WO | 2009021726 A1 | 2/2009 |
| WO | 2013017497 A1 | 2/2013 |

OTHER PUBLICATIONS

International Search Report and Written Opinion from PCT/US2014/068607 dated Mar. 5, 2015.
International Search Report and Written Opinion from PCT/US2014/068503 dated Apr. 1, 2015.
International Search Report and Written Opinion from PCT/US2014/068512 dated Apr. 1, 2015.
International Search Report and Written Opinion from PCT/US2014/068506 dated Apr. 8, 2015.
International Search Report and Written Opinion from PCT/US2014/068515 dated Apr. 10, 2015.
Eastwood, S.C., et al., "Pilot Plants: Thermofor Catalytic Cracking Unit", Industrial and Engineering Chemistry, Dec. 1947, pp. 1685-1690, vol. 39, No. 12, ACS Publications.
Chang et al., "The Conversion of Methanol and Other O-Compounds to Hydrocarbons over Zeolite Catalysts", Journal of Catalysis, 1977, pp. 249-259, vol. 47, Academic Press.
Ono et al., "Selective conversion of methanol into aromatic hydrocarbons over zinc-exchanged ZSM-5 zeolites," Journal of the Chemical Society, Faraday Transactions 1, Jan. 1988, p. 1091, vol. 84, No. 4, Royal Society of Chemistry.
Wolterman, G.W., et al., "Chapter 4 Commercial Preparation and Characterization of FCC Catalysts", Studies in Surface Science and Catalysis, 1993, pp. 105-144, vol. 76, Elsevier.
Inque et al., "Selective conversion of methanol into aromatic hydrocarbons over silver-exchanged ZSM-5 zeolites," Microporous Materials, Aug. 1995, pp. 379-383, vol. 4, No. 5, Elsevier.
International Search Report and Written Opinion from PCT/US2014/068508 dated Feb. 17, 2015.
International Search Report and Written Opinion from PCT/US2014/068509 dated Feb. 25, 2015.

* cited by examiner

CATALYST FOR CONVERSION OF OXYGENATES TO AROMATICS

CROSS-REFERENCE TO RELATED APPLICATIONS

This application claims the benefit of U.S. Provisional Application Nos. 61/918,984, 61/918,994, and 61/919,013, each filed on Dec. 20, 2013, the entire contents of each of which are hereby incorporated by reference herein.

FIELD OF THE INVENTION

The invention relates to zeolite-containing compositions and methods of making such compositions. The compositions may be used as catalysts, e.g., for the conversion of oxygenates to aromatic hydrocarbons.

BACKGROUND OF THE INVENTION

A variety of industrial processes are known for conversion of low boiling carbon-containing compounds to higher value products. One such process converts methanol to gasoline (MTG) using ZSM-5 zeolite catalysts. In the MTG process, methanol is first dehydrated to dimethyl ether. The methanol and/or dimethyl ether are then converted in a series of reactions that results in formation of a hydrocarbon mixture that comprises aromatic, paraffinic, and olefinic compounds. This mixture may be separated into a liquefied petroleum gas (LPG) fraction and a high-quality gasoline fraction comprising aromatics, paraffins, and olefins. The typical MTG hydrocarbon product consists of about 10-20% olefins and about 40-50% paraffins and 40-50% aromatics, e.g., xylenes, benzene, toluene, etc.

U.S. Pat. Nos. 6,423,879 and 6,504,072 disclose processes for the selective production of para-xylene which comprises reacting toluene with methanol in the presence of a catalyst comprising a porous crystalline material having a Diffusion Parameter for 2,2 dimethylbutane of about 0.1-15 $sec^{-1}$ when measured at a temperature of 120° C. and a 2,2 dimethylbutane pressure of 60 torr (8 kPa). The porous crystalline material is preferably a medium-pore zeolite, particularly ZSM-5, which has been severely steamed at a temperature of ≥950° C. and which has been combined with about 0.05 to about 20 wt % of at least one oxide modifier, preferably an oxide of phosphorus, to control reduction of the micropore volume of the material during the steaming step. The porous crystalline material is normally combined with a binder or matrix material, preferably silica or a kaolin clay.

U.S. Pat. No. 7,304,194 discloses a process for the hydrothermal treatment of a phosphorus-modified ZSM-5 catalyst. In the process, ZSM-5 having a silica/alumina mole ratio of ≥about 250 and a phosphorus content of from ≥about 0.08 g P/g zeolite to about 0.15 g P/g zeolite is calcined at a temperature of ≥300° C. and then contacted with steam at a temperature of from about 150° C. to about 250° C. The steamed, phosphorus modified zeolite is said to exhibit improved para-selectivity and methanol selectivity when used as a catalyst in toluene methylation reactions. The steamed, phosphorus modified zeolite may be used as a catalyst in unbound form or in combination with a binder material, such as alumina, clay, and silica.

In addition, U.S. Pat. No. 7,285,511 discloses a process of modifying a zeolite catalyst to increase its para-xylene selectivity in toluene methylation reactions, wherein the method comprises forming a slurry consisting essentially of a binder-free ZSM-5-type zeolite having a $SiO_2/Al_2O_3$ mole ratio of from about 250 to about 1000 and an aqueous solution of a phosphorus-containing compound; and removing water from the slurry to provide a non-steamed, phosphorus treated ZSM-5 zeolite having a phosphorus content of from 0.04 g P/g zeolite or more and a pore volume of from 0.2 ml/g or less. The resultant phosphorus treated ZSM-5 can be used as a toluene methylation catalyst either in unbound form or may be composited with a binder, such as alumina, clay, or silica.

Phosphorus modification is a known method of improving the performance of zeolite catalysts for a variety of chemical processes including, for example, the conversion of methanol to hydrocarbons and the methylation of toluene to produce xylenes. For example, U.S. Pat. Nos. 4,590,321 and 4,665,251 disclose a process for producing aromatic hydrocarbons by contacting one or more non-aromatic compounds, such as propane, propylene, or methanol, with a catalyst containing a zeolite, such as ZSM-5, together with a binder or matrix material resistant to the temperature and other conditions employed in the process. The zeolite is modified with phosphorus oxide by impregnating the zeolite with a source of phosphate ions, such as an aqueous solution of an ammonium phosphate, followed by calcination. The phosphorus oxide modification is said to render the zeolite more active and/or benzene selective in the aromatization reaction.

Nevertheless, there is still a need for catalyst compositions having improved selectivity and/or resistance to deactivation and/or persistence in the selectivity of aromatic selectivity.

SUMMARY OF THE INVENTION

It has been found that one or more of the above needs may be provided by zeolite-containing catalyst compositions enhanced by the presence of a Group 10-12 and a Group 15 element. Such catalysts typically have a high selectivity for desirable aromatic molecules while providing improved catalyst lifetime.

Thus, in one aspect, embodiments of the invention provide a catalyst composition comprising: a zeolite having a molar ratio of silicon to aluminum of about 10.0 to about 300.0; a Group 10-12 element and combinations thereof; a Group 15 element and combinations thereof; and optionally, a binder, wherein the catalyst composition has a molar ratio of Group 15 element to Group 10-12 element of about 0.01 to about 10.0.

In another aspect, embodiments of the invention provide a catalyst composition comprising an aluminosilicate zeolite, zinc, phosphorus, and optionally a binder, the zeolite having a molar ratio of silicon to aluminum of ≥about 10.0 to about 300.0, the catalyst composition comprising 0 to about 80.0 wt % binder, based on a total weight of the catalyst composition and having a micropore surface area of ≥about 100 $m^2/g$, a molar ratio of zinc to aluminum of about 0.1 to about 1.3, a molar ratio of phosphorus to zinc of 0.01 to 10.0 and at least one of: (a) a mesoporous surface area of about 20.0 to about 500.0 $m^2/g$; and (b) a diffusivity for 2,2-dimethylbutane of $1.25\times10^{-2}$ to $3.00\times10.2$ $sec^{-1}$, when measured at a temperature of about 120° C. and a 2,2-dimethylbutane pressure of about 60 torr (about 8 kPa).

In still another aspect, embodiments of the invention provide a method for organic compound conversion, comprising exposing a first mixture comprising ≥10.0 wt % of at least one oxygenate, based on the weight of the first mixture, to a catalyst composition comprising: an aluminosilicate zeolite, zinc, phosphorus, and optionally a binder, the zeolite having a molar ratio of silicon to aluminum of about 10.0 to about 300.0, 0 to about 80.0 wt % binder, based on a total weight of the catalyst composition and having a micropore surface area of ≥about 100 m²/g, a molar ratio of zinc to aluminum of about 0.1 to about 1.3, a molar ratio of phosphorus to zinc of 0.01 to 10.0 and at least one of: (a) a mesoporous surface area of about 20 to about 500 m²/g, and (b) a diffusivity for 2,2-dimethylbutane of $1.25 \times 10^{-2}$ to $3.00 \times 10^{-2}$ sec$^{-1}$ when measured at a temperature of about 120° C. and a 2,2-dimethylbutane pressure of about 60 torr (about 8 kPa); said exposing being conducted under conditions effective to covert at least a portion of the first mixture into a hydrocarbon containing stream comprising one or more aromatic hydrocarbons, the method being characterized by a deactivation ratio, DR, of ≤15 wt % after processing 200.0 to 400 g of oxygenate per gram of the catalyst composition, wherein DR is defined as:

$$DR = \frac{|(A_{200-400} - A_{initial})|}{A_{initial}} * 100\%$$

where $A_{initial}$ is defined as the initial selectivity to aromatics (on a weight % of hydrocarbon product basis) at the beginning of oxygenate processing, and $A_{200-400}$ is defined as the selectivity to aromatics (on the same basis) after processing 200 to 400 grams of oxygenate per gram of catalyst composition.

In still another aspect, embodiments of the invention provide a method for organic compound conversion, comprising providing a first mixture, the first mixture comprising ≥10.0 wt % oxygenate based on the weight of the first mixture; exposing at a temperature ≥300° C. and at a pressure ≥1 bara a catalyst composition to the first mixture to convert at least a portion of the oxygenate to hydrocarbons, the hydrocarbons comprising ≥50.0 wt % of aromatics, based on the weight of the hydrocarbons, wherein the catalyst composition comprises a zeolite having a molar ratio of silicon to aluminum of 10.0 to 300.0; a Group 12 element selected from the group consisting of Zn, Cd, and combinations thereof; a Group 15 element selected from the group consisting of phosphorus, arsenic, antimony, bismuth, and combinations thereof; and optionally a binder, wherein the catalyst composition has a molar ratio of Group 15 element to Group 12 element of about 0.01 to about 10.0.

DETAILED DESCRIPTION

For the purposes of this invention and the claims thereto, the numbering scheme for the Periodic Table Groups is used as described in Chemical and Engineering News, 63(5), pg. 27 (1985).

In various aspects, a zeolite catalyst composition is provided, along with methods for use of the catalyst for the conversion of oxygenate feeds to aromatics, olefins, and paraffins with high aromatics yield and/or reduced catalyst deactivation. While some catalyst compositions include a binder, in some cases, the catalyst composition may be referred to as being "self-bound" or "unbound." The terms "unbound" and "self-bound" are intended to be synonymous and mean that such a catalyst composition is free of any inorganic oxide binders, such as alumina or silica, frequently combined with zeolite catalysts to enhance their physical properties.

The zeolite employed in the present catalyst composition generally comprises at least one medium pore aluminosilicate zeolite or silica aluminophosphate (SAPO) having a Constraint Index of 1-12. The Constraint Index may be ≤about 12.0, ≤about 11.0, ≤about 10.0, ≤about 9.0, ≤about 8.0, ≤about 7.0, ≤about 6.0, ≤about 5.0, ≤about 4.0, ≤about 3.0, or ≤about 2.0. Additionally or alternatively, the Constraint Index may be about ≥about 11.0, ≥about 10.0, ≥about 9.0, ≥about 8.0, ≥about 7.0, ≥about 6.0, ≥about 5.0, ≥about 4.0, ≥about 3.0, ≥about 2.0, or ≥about 1.0. In any embodiment, the Constraint Index may be 1.0 to about 10.0, 1.0 to about 8.0, 1 to about 6.0, 1 to about 5.0, 1 to about 3.0, 2.0 to about 11.0, 3.0 to 10.0, 4.0 to 9.0, or 6.0 to 9.0, etc. Constraint Index is determined as described in U.S. Pat. No. 4,016,218, incorporated herein by reference for details of the method.

Some useful catalysts compositions can include a zeolite having a structure wherein there is at least one 10-member ring channel and no channel of rings having more than 10 members. Some such molecular sieves may be referred to as having a framework type or topology of EUO, FER, IMF, LAU, MEL, MRI, MFS, MTT, MWW, NES, PON, SFG, STF, STI, TUN, or PUN. Particularly useful zeolites can have a BEA, MFI or MEL framework.

Non-limiting examples of SAPOs useful herein can include one or a combination of SAPO-5, SAPO-8, SAPO-11, SAPO-16, SAPO-17. SAPO-18, SAPO-20, SAPO-31, SAPO-34, SAPO-35, SAPO-36, SAPO-37, SAPO-40, SAPO-41, SAPO-42, SAPO-44, SAPO-47, and SAPO-56.

Particular other zeolites useful in embodiments of the invention can include ZSM-5, ZSM-11; ZSM-12; ZSM-22; ZSM-23; ZSM-34, ZSM-35; ZSM-48; ZSM-57; and ZSM-58. Other useful zeolites may include MCM-22, PSH-3, SSZ-25, MCM-36, MCM-49 or MCM-56, with MCM-22. In any embodiment the zeolite may be ZSM-5 or ZSM-11. ZSM-5 is described in detail in U.S. Pat. No. 3,702,886 and U.S. Pat. No. RE 29,948. ZSM-11 is described in detail in U.S. Pat. No. 3,709,979. ZSM-5 can be particularly useful.

Generally, a zeolite having the desired activity can have a silicon to aluminum molar ratio of about 10.0 to about 300.0. In any embodiment, the molar ratio of silicon to aluminum may be ≤about 300.0, ≤about 200.0, ≤about 150.0, ≤about 125.0, ≤about 100.0, ≤about 80.0, ≤about 60.0, ≤about 50.0, ≤about 40.0, ≤about 30.0, ≤about 25.0, ≤about 20.0, ≤about ≤15.0 or about ≤10.0. Additionally or alternatively, the molar ratio of silicon to aluminum may be ≥about 10.0, ≥about 15.0, ≥about 20.0, ≥about 25.0, ≥about 30.0, ≥about 40.0, ≥about 50.0, ≥about 60.0, ≥about 80.0, ≥about 100.0, ≥about 125.0, ≥about 150.0, or ≥about 200.0; e.g., 20.0 to about 200.0, about 30.0 to about 100.0, about 40.0 to about 80.0, about 50.0 to about 50.0, about 15.0 to about 100.0, or about 20.0 to about 40.0.

Typically, reducing the molar ratio of silicon to aluminum in a zeolite can result in a zeolite with a higher acidity, and therefore in higher activity for cracking of hydrocarbon or hydrocarbonaceous feeds, such as petroleum feeds. However, with respect to conversion of oxygenates to aromatics, such increased cracking activity may not be beneficial, and instead may result in increased formation of residual carbon or coke during the conversion reaction. Such residual carbon can deposit on the zeolite catalyst, leading to deactivation of the catalyst over time. Having a molar ratio of silicon to aluminum of ≥about 40.0, such as ≥about 50.0 or ≥about 60.0, can reduce and/or minimize the amount of additional residual carbon formed due to the acidic or cracking activity of the catalyst.

It is noted that the molar ratio described herein is a ratio of silicon to aluminum. If a corresponding ratio of silica to alumina is described, the corresponding ratio of silica ($SiO_2$) to alumina ($Al_2O_3$) would be twice as large, due to the presence of two aluminum atoms in each alumina stoichiometric unit. Thus, a molar ratio of silicon to aluminum of 10.0 corresponds to a silica to alumina ratio of 20.0.

When used in the present catalyst compositions, the zeolite can be present at least partly in the hydrogen (acid) form. Depending on the conditions used to synthesize the zeolite, this may correspond to converting the zeolite from, for example, the sodium form. This can readily be achieved, for example, by ion exchange to convert the zeolite to the ammonium form followed by calcination in air or an inert atmosphere at a temperature of about 400° C. to about 700° C. to convert the ammonium form to the active hydrogen form.

Zeolite catalyst compositions can include and/or be enhanced by a transition metal. Catalyst compositions herein include a Group 10-12 element or combinations thereof, of the Periodic Table. Exemplary Group 10 elements include, nickel, palladium, and/or platinum, particularly nickel. Exemplary Group 11 elements include copper, silver, and/or gold, particularly copper. Exemplary Group 12 elements include e.g., zinc and/or cadmium. In particular embodiments, nickel, copper and/or zinc, particularly zinc, may be used. The Group 10-12 element can be incorporated into the zeolite by any convenient method, such as by impregnation or by ion exchange. After impregnation or ion exchange, the Group 10-12 element-enhanced catalyst can be treated in an oxidizing environment (air) or an inert atmosphere at a temperature of about 400° C. to about 700° C.

The amount of Group 10-12 element can be related to the molar amount of aluminum present in the zeolite. Preferably, the molar ratio of the Group 10-12 element to aluminum in the zeolite can be about 0.1 to about 1.3. For example, the molar ratio of the Group 10-12 element to aluminum in the zeolite can be about ≥0.1, e.g., ≥about 0.2, ≥about 0.3, or ≥about 0.4. Additionally or alternately, the molar ratio of the Group 10-12 element to aluminum in the zeolite can be about ≤1.3, such as about ≤1.2, ≤about 1.0, or ≤about 0.8. In any embodiment, the ratio of the Group 10-12 element to aluminum is about 0.2 to about 1.2, about 0.3 to about 1.0, or about 0.4 to about 0.8. Still further additionally or alternately, the amount of Group 10-12 element can be expressed as a weight percentage of the self-bound or unbound zeolite, such as having ≥about 0.1 wt %, ≥about 0.25 wt %, ≥about 0.5 wt %, ≥about 0.75 wt %, or ≥about 1.0 wt % of Group 10-12 element. Additionally or alternatively, the amount of Group 10-12 element can be present in an amount of ≤about 20 wt %, such as ≤about 10 wt %, ≤about 5 wt %, ≤about 2.0 wt %, ≤about 1.5 wt %, ≤about 1.2 wt %, ≤about 1.1 wt %, or ≤about 1.0 wt %. In any embodiment, the amount of Group 10-12 element may be about 0.25 to about 10.0 wt %, about 0.5 to about 5.0 wt %, about 0.75 to about 2.0 wt %, or about 1.0 to about 1.5 wt %, based on the total weight of the catalyst composition excluding the weight of any binder if present.

Typically, the catalyst compositions herein also include a Group 15 element, e.g., phosphorus, arsenic, antimony, bismuth, and combinations thereof in addition to the transition metal. In any embodiment, the Group 15 element may be phosphorus.

The Group 15 element can be incorporated into the catalyst composition in any of the same manners described for incorporation of the Group 10-12 element. Any source of convenient source of the Group 15 element may be used, e.g., phosphoric acid ($H_3PO_4$) or ammonium dihydrogen phosphate ($NH_4H_2PO_4$). Typically, the catalyst composition has a molar ratio of Group 15 to Group 10-12 element of about 0.1 to about 10.0. In any embodiment, the molar ratio of Group 15 to Group 10-12 element may be ≤about 10.0, ≤about 9.0, ≤about 8.0, ≤about 7.0, ≤about 6.0, ≤about 5.0, ≤about 4.0, ≤about 3.0, ≤about 2.5, ≤about 1.0, ≤about 0.5, ≤about 0.4, ≤about 0.3, ≤about 0.2, or ≤about 0.1. Additionally or alternatively, the molar ratio of Group 15 to Group 10-12 element may be ≥about 0.1, ≥about 0.2, ≥about 0.3, ≥about 0.4, ≥about 0.5, ≥about 1.5, ≥about 2.0, ≥about 3.0, ≥about 4.0, ≥about 5.0, ≥about 6.0, ≥about 7.0, ≥about 8.0, ≥about 9.0, or ≥about 10.0. Ranges of the molar ratio of Group 15 to Group 10-12 element expressly disclosed include combinations of any of the above-enumerated upper and lower limits, e.g., about 0.2 to about 9.0, about 0.4 to about 8.0, about 0.6 to about 6.0, about 0.8 to about 4.0, about 1.0 to about 3.0, about 1.5 to about 2.5, etc. Additionally or alternatively, the amount of Group 15 element can be present in an amount of about ≤5.0 wt %, such as ≤about 2.5 wt %, ≤about 1.0 wt %, ≤about 0.75 wt %, ≤about 0.50 wt %, ≤about 0.25 wt %, or ≤about 0.1 wt %. In any embodiment, the amount of Group 15 element may be about 0.1 to about 5.0.0 wt %, about 0.25 to about 2.0 wt %, about 0.5 to about 1.0 wt %, or about 1.0 wt %, based on the total weight of the catalyst composition excluding the weight of any binder if present. Where the zeolite is a SAPO and the Group 15 element includes phosphorus, the molar amounts and weight percentages of the phosphorus recited in this paragraph shall exclude the amount of phosphorus attributed to the SAPO zeolite.

Additionally or alternatively, the catalyst compositions may also include at least one Group 2 and/or a Group 3 element. As used herein the term "Group 3" is intended to include elements in the Lanthanide series of the Periodic Table. In any embodiment, one or more Group 2 elements (e.g., Be, Mg, Ca, Sr, Ba, and/or Ra) may be used. In other embodiments, one or more Group 3 elements (e.g., Sc and/or Y), a Lanthanide (e.g., La, Ce, Pr, Nd, Sm, Eu, Gd, Tb, Dy, Ho, Er, Tm, Yb, and/or Lu). While an Actinide may be used, such elements are not believed to offer any particular advantage. When present, the total weight of the at least one Group 2 and/or Group 3 elements is from about 0.1 to about 20.0 wt %, based on the total weight of the catalyst composition excluding the weight of any binder if present. In any embodiment, the amount of the at least one Group 2 and/or a Group 3 element may be about 0.25 to about 10.0 wt %, about 0.5 to about 5.0 wt %, about 0.75 to about 2.0 wt %, or about 1.0 to about 1.5 wt %. The presence of Group 2 and/or Group 3 element is believed to reduce coke formation.

The catalyst composition can employ the zeolite in its original crystalline form or after formulation into catalyst particles, such as by extrusion. A process for producing zeolite extrudates in the absence of a binder is disclosed in, for example, U.S. Pat. No. 4,582,815, the entire contents of which are incorporated herein by reference. Preferably, the Group 15 element, the Group 10-12 element, and/or the at least one Group 2 and/or Group 3 element can be incorporated after formulation of the zeolite (such as by extrusion) to form self-bound catalyst particles. Optionally, a self-bound catalyst can be steamed after extrusion.

Thus, embodiments of the catalyst compositions described herein can further be characterized by at least one, at least two, or all of the following properties: (a) a mesoporosity (i.e., mesoporous surface area or surface area external to the zeolite) of ≥about 20.0 m$^2$/g, e.g., ≥about 30.0 m$^2$/g, ≥about 40.0 m$^2$/g, ≥about 50.0 m$^2$/g, ≥about 60.0 m$^2$/g, ≥about 70.0 m$^2$/g, ≥about 80.0 m$^2$/g, ≥about 90.0 m$^2$/g, ≥about 100.0 m$^2$/g, or ≥about 200.0 m$^2$/g. Additionally or alternatively, the mesoporous surface area may be ≤about 500.0 m$^2$/g, e.g., ≤about 400.0 m$^2$/g, ≤about 300.0 m$^2$/g, ≤about 200.0 m$^2$/g, or ≤about 100.0 m$^2$/g. Exemplary such ranges for the mesoporous surface are include about 20.0 to 500.0 m$^2$/g, about 20.0 to about 400.0 m$^2$/g, about 20.0 to about 300.0 m$^2$/g, about 20.0 to about 200.0 m$^2$/g, about 20.0 to about 100.0 m$^2$/g, about 20.0 to about 90.0 m$^2$/g, about 20.0 to about 80.0 m$^2$/g, about 20.0 to about 70.0 m$^2$/g, about 20.0 to about 60.0 m$^2$/g, about 20.0 to about 50.0 m$^2$/g, about 30.0 to about 200.0 m$^2$/g, about 30.0 to about 100.0 m$^2$/g, about 40.0 to about 100.0 m$^2$/g, about 50.0 to about 100.0 m$^2$/g, about 60.0 to about 100.0 m$^2$/g, about 70.0 to about 100.0 m$^2$/g, etc.; (b) a microporous surface area of ≥about 100.0 m$^2$/g, e.g., ≥about 200.0 m$^2$/g, ≥about 300.0 m$^2$/g, ≥about 340.0 m$^2$/g, ≥about 350.0 m$^2$/g, ≥about 360.0 m$^2$/g, or ≥about 370.0 m$^2$/g. Additionally or alternatively, the microporous surface area may be ≤about 1000.0 m$^2$/g, e.g., ≤about 750.0 m/g, ≤about 600.0 m$^2$/g, or ≤about 500.0 m$^2$/g. Exemplary such ranges include about 100.0 to about 1000.0 m$^2$/g, about 200.0 to about 1000.0 m$^2$/g, about 300 to about 1000.0 m$^2$/g, about 340.0 to about 1000.0 m$^2$/g, about 350.0 to about 1000.0 m$^2$/g, about 360.0 to about 1000.0 m$^2$/g, about 370.0 to about 1000.0 m$^2$/g, about 100.0 to about 750.0 m$^2$/g, about 200.0 to about 750.0 m$^2$/g, about 300.0 to about 750.0 m$^2$/g, about 340.0 to about 750.0 m$^2$/g, about 350.0 to about 750.0 m$^2$/g, about 360.0 to about 750.0 m$^2$/g, about 370.0 to about 750.0 m$^2$/g, about 360.0 to about 600.0 m$^2$/g, or about 350 to about 500.0 m$^2$/g, etc.; and/or (c) a diffusivity for 2,2-dimethylbutane of ≥about 1.0×10$^{-2}$ sec$^{-1}$, e.g., ≥about 1.10×10$^{-2}$ sec$^{-1}$, ≥about 1.15×10$^{-2}$ sec$^{-1}$, ≥about 1.20×10$_{-2}$ sec$^{-1}$, ≥about 1.25×10$^{-2}$ sec$^{-1}$, or ≥about 1.50×10$^{-2}$ sec$^{-1}$ Additionally or alternatively, the diffusivity for 2,2-dimethylbutane may be ≤about 3.00×10$^{-2}$ sec$^{-1}$, ≤about 2.75×10$^{-2}$ sec$^{-1}$, ≤about 2.50×10$^{-2}$ sec$^{-1}$ or ≤about 2.00×10$^{-2}$ sec$^{-1}$. Exemplary such ranges include about 1.0×10$^{-2}$ sec$^{-1}$ to about 3.00×10$^{-2}$ sec$^{-1}$, about 1.25×10$^{-2}$ to about 3.00×10$^{-2}$ sec$^{-1}$, about 1.50×10$^{-2}$ to about 2.00×10$^{-2}$ sec$^{-1}$, etc., when measured at a temperature of about 120° C. and a 2,2-dimethylbutane pressure of about 60 torr (about 8 kPa).

Of these properties, mesoporosity and diffusivity for 2,2-dimethylbutane are determined by a number of factors for a given zeolite, including the crystal size of the zeolite. Microporous surface area is determined by the pore size of the zeolite and the availability of the zeolite pores at the surfaces of the catalyst particles. Producing a zeolite catalyst with the desired low (minimum) mesoporosity, microporous surface area, and 2,2-dimethylbutane diffusivity would be well within the expertise of one of ordinary skill in zeolite chemistry. It is noted that mesopore surface area and micropore surface area can be characterized, for example, using adsorption-desorption isotherm techniques within the expertise of one of skill in the art, such as the BET (Brunauer Emmet Teller) method.

It is noted that the micropore surface area can be characterized for zeolite crystals or a catalyst formed from the zeolite crystals. In various aspects, the micropore surface area of a self-bound catalyst or a catalyst formulated with a separate binder can be ≥about 100.0 m$^2$/g, e.g., ≥about 200.0 m$^2$/g, ≥about 300.0 m$^2$/g, ≥about 340.0 m$^2$/g, ≥bout 350.0 m$^2$/g, ≥bout 360.0 m$^2$/g, or ≥about 370.0 m$^2$/g. Additionally or alternatively, the microporous surface area may be ≤about 1000.0 m$^2$/g, e.g., ≤about 750.0 m$^2$/g, ≥bout 600.0 m$^2$/g, or ≥about 500.0 m$^2$/g. Exemplary such ranges include about 100.0 to about 1000.0 m$^2$/g, about 200.0 to about 1000.0 m$^2$/g, about 300 to about 1000.0 m$^2$/g, about 340.0 to about 1000.0 m$^2$/g, about 350.0 to about 1000.0 m$^2$/g, about 360.0 to about 1000.0 m$^2$/g, about 370.0 to about 1000.0 m$^2$/g, about 100.0 to about 750.0 m$^2$/g, about 200.0 to about 750.0 m$^2$/g, about 300.0 to about 750.0 m$^2$/g, about 340.0 to about 750.0 m$^2$/g, about 350.0 to about 750.0 m$^2$/g, about 360.0 to about 750.0 m$^2$/g, about 370.0 to about 750.0 m$^2$/g, about 360.0 to about 600.0 m$^2$/g, or about 350 to about 500.0 m$^2$/g, etc. Typically, a formulation of zeolite crystals into catalyst particles (either self-bound or with a separate binder) can result in some loss of micropore surface area relative to the micropore surface area of the zeolite crystals. Thus, in order to provide a catalyst having the desired micropore surface area, the zeolite crystals can also have a micropore surface area of ≥about 100.0 m$^2$/g, e.g., ≥about 200.0 m$^2$/g, ≥about 300.0 m$^2$/g, ≥about 340.0 m$^2$/g, ≥about 350.0 m$^2$/g, ≥about 360.0 m$^2$/g, or ≥about 370.0 m$^2$/g. Additionally or alternatively, the microporous surface area may be ≤about 1000.0 m$^2$/g, e.g., ≤about 750.0 m$^2$/g, ≤about 600.0 m$^2$/g, or ≤about 500.0 m$^2$/g. Exemplary such ranges include about 100.0 to about 1000.0 m$^2$/g, about 200.0 to about 1000.0 m$^2$/g, about 300 to about 1000.0 m$^2$/g, about 340.0 to about 1000.0 m$^2$/g, about 350.0 to about 1000.0 m$^2$/g, about 360.0 to about 1000.0 m$^2$/g, about 370.0 to about 1000.0 m$^2$/g, about 100.0 to about 750.0 m$^2$/g, about 200.0 to about 750.0 m g, about 300.0 to about 750.0 m$^2$/g, about 340.0 to about 750.0 m/g, about 350.0 to about 750.0 m$^2$/g, about 360.0 to about 750.0 m$^2$/g, about 370.0 to about 750.0 m$^2$ g, about 360.0 to about 600.0 m$^2$/g, or about 350 to about 500.0 m$^2$ g, etc. As a practical matter, the micropore surface area of a zeolite crystal and/or a corresponding self-bound or bound catalyst as described herein can be ≤about 1000 m$^2$/g, and typically ≤about 750 m$^2$/g. Additionally or alternatively, the micropore surface area of a catalyst (self-bound or with a separate binder) can be ≤about 105% of the micropore surface area of the zeolite crystals in the catalyst, and typically ≤about 100% of the micropore surface area of the zeolite crystals in the catalyst, such as from about 80% to about 100% of the micropore surface area of the zeolite crystals in the catalyst. For example, the micropore surface area of a catalyst can be ≥about 80% of the micropore surface area of the zeolite crystals in the catalyst, such as ≥about 85%, ≥about 90%, ≥about 95%, ≥about 97%, or ≥about 98%, and/or ≤about 100%, ≤about 99%, ≤about 98%, ≤about 97%, or ≤about 95%.

Additionally or alternatively, the diffusivity for 2,2-dimethylbutane of a catalyst composition (self-bound or with a separate binder) can be ≤about 105.0% of the diffusivity for 2,2-dimethylbutane of the zeolite crystals in the catalyst, and typically ≤about 100.0% or of the diffusivity for 2,2-dimethylbutane of the zeolite crystals in the catalyst, such as from about 80.0% to about 100.0% of the diffusivity for 2,2-dimethylbutane of the zeolite crystals in the catalyst. For example, the diffusivity for 2,2-dimethylbutane of a catalyst can be ≥about 80.0% of the diffusivity for 2,2-dimethylbutane of the zeolite crystals in the catalyst, such as ≥about 85.0%, ≥about 90.0%, ≥about 95.0%, ≥about 97.0%, or ≥about 98.0%, and/or ≤about 100.0%, ≤about 99.0%, ≤about 98.0%, ≤about 97.0%, or ≤about 95.0%.

Additionally or alternatively, the catalyst composition comprises particles having a size ≥about 0.01 μm, ≥about 0.05 μm, ≥about 0.08 μm, ≥about 0.10 μm, ≥about 0.20 μm, or ≥about 0.50 μm. Likewise, the catalyst composition may comprise particles wherein the upper limit is ≤about 0.6 μm, ≤about 0.5 μm, ≤about 0.4 μm, ≤about 0.3 μm, ≤about 0.2 μm, ≤about 0.1 μm, or ≤about 0.05 μm. In any embodiment, the catalyst may comprise particles having a size of about 0.01 μm to about 0.6 μm, 0.02 to 0.50 μm, 0.03 to 0.40 μm etc. As used herein the term "size" means either the diameter of approximately spherical particles or, where a particle has another shape, the average of the longest dimension and the dimension orthogonal thereto. Particle dimensions and size can be determined by any suitable means, typically microscopically, using a representative number of particles. "Size" may refer to self-bound particles or particles including a binder, or those formed by extrusion of other method.

Additionally or alternatively, catalyst compositions herein may be described by a particle size distribution, $D_x$, ≤about 1.0 μm, ≤about 0.5 μm, ≤about 0.40 μm, ≤about 0.20 μm, ≤about 0.10 μm, ≤about 0.05 μm, or ≤about 0.01 μm, where x is 50.0, 90.0, or 95.0. The particle size distribution, may also be ≥about 1.0 μm, ≥about 0.8 μm, ≥about 0.5 μm, ≥about 0.20 μm, ≥about 0.10 μm, ≥about 0.05 μm, ≥about 0.01 μm. In any embodiment, the particle size distribution, $D_x$, may be 0.01 to 0.60 μm, 0.02 to 0.50 μm, 0.03 to 0.40 μm, 0.01 to 0.05 μm, 0.10 to 0.60 μm, 0.2 to 0.5 μm, or 0.3 to 0.4 μm. The particle size distribution, $D_x$, means that at least x number percent of the particles have a size, as defined above, in the recited range. For example, a catalyst composition described as having a $D_{90.0}$ of 0.10 to 0.60 means that at least 90.0 number percent of the particles have a size between 0.10 and 0.60 μm. In any embodiment, the particle size may be relatively narrow, i.e., $D_{90.0}$ or $D_{95.0}$ may be preferred, i.e., a $D_{90.0}$ or $D_{95.0}$ of ≤about 1 μm, ≤about 0.5 μm, or ≤about 0.4 μm, 0.01 to 0.60 μm, 0.02 to 0.50 μm, 0.03 to 0.40 μm, 0.01 to 0.05 μm, 0.10 to 0.60 μm, 0.2 to 0.5 μm, or 0.30 to 0.40 μm.

In some aspects, the catalyst composition can have an alpha value of at least about 10.0, such as at least about 20.0 or at least about 50.0. Additionally or alternatively, the catalyst composition can have an alpha value of ≤about 1000.0, ≤about 800.0, ≤about 700.0, or ≤about 600.0; e.g., about 10.0 to about 1000.0, about 10.0 to about 800.0, or about 50.0 to 700.0. The alpha value of a catalyst composition is a measure of the acid activity of a zeolite catalyst as compared with a standard silica-alumina catalyst. The alpha test is described in U.S. Pat. No. 3,354,078; in the Journal of Catalysis at vol. 4, p. 527 (1965), vol. 6, p. 278 (1966), and vol. 61, p. 395 (1980), each incorporated herein by reference as to that description. The experimental conditions of the test used herein include a constant temperature of about 538° C. and a variable flow rate as described in detail in the Journal of Catalysis at vol. 61, p. 395. The higher alpha values correspond with a more active cracking catalyst.

As an alternative to forming self-bound catalysts, zeolite crystals can be combined with a binder to form bound catalyst compositions containing a relatively small amount of binder. Suitable binders for zeolite-based catalysts can include various inorganic oxides, such as silica, alumina, zirconia, titania, silica-alumina, cerium oxide, magnesium oxide, or combinations thereof. Generally, a binder can be present in an amount of 0 to about 80.0 wt %, ≤about 65.0 wt %, ≤about 40.0 wt %, ≤about 35.0 wt %, ≤about 25.0 wt %, or ≤20.0 wt %, based on the total weight of the catalyst composition. Additionally or alternatively, the binder may in any embodiment be present in an amount of 0 wt %, ≥about 1.0 wt %, ≥about 5.0 wt %, ≥about 10.0 wt %, or ≥about 15.0 wt %, e.g., 0 to about 80.0 wt %, about 5.0 to about 40.0 wt %, about 10.0 to about 35.0, about 10.0 to about 25.0, or about 15.0 to about 20.0 wt %. In any embodiment, only a relatively small amount of binder may be present, e.g., an upper limit of about 5.0 wt %, about 2.5 wt %, or about 1.0 wt % and a lower limit of about 0.1 wt %, about 0.5 wt %, about 1.0 wt %, such as 0.1 to 5.0 wt %, 0.5 to 2.5 wt %, 0.5 to 1.0 wt %, or 0.1 to 1.0 wt %. Combining the zeolite and the binder can generally be achieved, for example, by mulling an aqueous mixture of the zeolite and binder and then extruding the mixture into catalyst pellets. A process for producing zeolite extrudates using a silica binder is disclosed in, for example, U.S. Pat. No. 4,582,815. Optionally, a bound catalyst can be steamed after extrusion.

In some aspects, a binder can be used that is substantially free of alumina, such as a binder that is essentially free of alumina. In this description, a binder that is substantially free of alumina is defined as a binder than contains ≤about 10.0 wt % alumina, such as ≤about 7.0 wt %, ≤about 5.0 wt %, or ≤about 3.0 wt %. A binder that is essentially free of alumina is defined as a binder that contains ≤about 1.0 wt %, such as about ≤0.5 wt %, or ≤about 0.1 wt %. Additionally or alternately, a binder can be used that contains no intentionally added alumina and/or that contains no alumina within conventional detection limits for determining the composition of the binder and/or the reagents for forming the binder. Although alumina is commonly used as a binder for zeolite catalysts, due in part to ease of formulation of alumina-bound catalysts, in some aspects the presence of alumina in the binder can reduce and/or inhibit the activity of a catalyst composition for converting methanol to aromatics. For example, for a catalyst where the Group 10-12 and/or Group 15 is incorporated into the catalyst after formulation of the bound catalyst (such as by extrusion), the Group 10-12 and/or Group 15 element may have an affinity for exposed alumina surfaces relative to exposed zeolite surfaces, leading to increased initial deposition and/or migration of such elements to regions of the bound catalyst with an alumina surface in favor of regions with a zeolite surface. Additionally or alternatively, alumina-bound catalysts can tend to have low micropore surface area, meaning that the amount of available zeolite surface available for receiving a Group 10-12 element and/or Group 15 element may be undesirably low.

An example of a suitable binder for forming bound catalysts with a desirable micropore surface area is a silica binder. Optionally but preferably, a suitable binder can be a binder with a surface area of ≤about 200.0 m$^2$/g, e.g., ≤about 175.0 m$^2$/g, or ≤about 150.0 m$^2$/g. Without being bound by any particular theory, it is believed that catalysts formed using high surface area binders (such as high surface area alumina binders) can have an increased tendency for deposited added element(s) to migrate to the binder, rather than remaining associated with the zeolite. Unless otherwise specified, the surface area of the binder is defined herein as the combined micropore surface area and mesopore surface area of the binder.

Feedstocks and Products

In various aspects, catalyst compositions described herein can be used for conversion of oxygen-containing organic compounds (i.e., "oxygenates") in hydrocarbon feed mixtures to aromatic and/or olefin and paraffin products. In such aspects, catalyst compositions described herein can resist deactivation while maintaining relatively high yield of aromatics. Thus, embodiments of the catalyst compositions described herein can convert at least a portion of a first mixture comprising an oxygenate to aromatic products.

Likewise, embodiments of the invention provides a method for organic compound conversion, comprising: providing a first mixture comprising ≥10.0 wt % oxygenate; and exposing at least a portion of the first mixture to a catalyst composition described herein under conditions effective to convert at least a portion of the oxygenate to a hydrocarbons, the hydrocarbons comprising ≥50.0 wt % of aromatics, based on the weight of the hydrocarbons.

As used herein the phrase "at least a portion of" means >0 to 100.0 wt % of the process stream or composition to which the phrase refers. Thus, the phrase "at least a portion of" may mean ≤about 1.0 wt %, ≤about 2.0 wt %, ≤about 5.0 wt %, ≤about 10.0 wt %, ≤about 20.0 wt %, ≤about 25.0 wt %, ≤about 30.0 wt %, ≤about 40.0 wt %, ≤about 50.0 wt %, ≤about 60.0 wt %, ≤about 70.0 wt %, ≤about 75.0 wt %, ≤about 80.0 wt %, ≤about 90.0 wt %, ≤about 95.0 wt %, ≤about 98.0 wt %, ≤about 99.0 wt %, or 100.0 wt %. Additionally or alternatively, the phrase "at least a portion of" can mean ≥about 1.0 wt %, ≥about 2.0 wt %, ≥about 5.0 wt %, ≥about 10.0 wt %, ≥about 20.0 wt %, ≥about 25.0 wt %, ≥about 30.0 wt %, ≥about 40.0 wt %, ≥about 50.0 wt %, ≥about 60.0 wt %, ≥about 70.0 wt %, ≥about 75.0 wt %, ≥about 80.0 wt %, ≥about 90.0 wt %, ≥about 95.0 wt %, ≥about 98.0 wt %, ≥about 99.0 wt %. Ranges expressly disclosed include combinations of any of the above-enumerated values, e.g., about 10.0 to 100.0 wt %, about 10.0 to about 98.0 wt %, about 2.0 to about 10.0 wt %, about 40.0 to about 60.0 wt %, etc.

As used herein the term "first mixture" means a hydrocarbon-containing composition including one or more oxygenates. Typically, the first mixture comprises ≥10.0 wt % of at least one oxygenate, based on the weight of the first mixture. In any embodiment, the amount of oxygenate(s) in the first mixture may be ≤about 10.0 wt %, ≤about 12.5 wt %, ≤about 15.0 wt %, ≤about 20.0 wt %, ≤about 25.0 wt %, ≤about 30.0 wt %, ≤about 35.0 wt %, ≤about 40.0 wt %, ≤about 45.0 wt %, ≤about 50.0 wt %, ≤about 55.0 wt %, ≤about 60.0 wt %, ≤about 65.0 wt %, ≤about 70.0 wt %, ≤about 75.0 wt %, ≤about 80.0 wt %, ≤about 85.0 wt %, ≤about 90.0 wt %, ≤about 95.0 wt %, ≤about 99.0 wt %, ≤about 99.5 wt %, or 100.0 wt %. Additionally or alternatively, the amount of oxygenate in the first mixture may be ≥about 10.0 wt %, ≥about 12.5 wt %, ≥about 15.0 wt %, ≥about 20.0 wt %, ≥about 25.0 wt %, ≥about 30.0 wt %, ≥about 35.0 wt %, ≥about 40.0 wt %, ≥about 45.0 wt %, ≥about 50.0 wt %, ≥about 55.0 wt %, ≥about 60.0 wt %, ≥about 65.0 wt %, ≥about 70.0 wt %, 75.0 wt %, ≥about 80.0 wt %, ≥about 85.0 wt %, ≥about 90.0 wt %, ≥about 95.0 wt %, ≥about 99.0 wt %, ≥about 99.5 wt %, or 100.0 wt %. Ranges expressly disclosed include combinations of any of the above-enumerated upper and lower limits, e.g., 10.0 to 100.0 wt %, 12.5 to 99.5 wt %, 20.0 to 90.0, 50.0 to 99.0 wt %, etc.

As used herein the term "oxygenate" refers to oxygen-containing compounds having 1 to about 50 carbon atoms, 1 to about 20 carbon atoms, 1 to about 10 carbon atoms, or 1 to about 4 carbon atoms. Exemplary oxygenates can include alcohols, ethers, carbonyl compounds, e.g., aldehydes, ketones and carboxylic acids, and mixtures thereof. Particular oxygenates can include one or a combination of methanol, ethanol, dimethyl ether, diethyl ether, methylethyl ether, di-isopropyl ether, dimethyl carbonate, dimethyl ketone, formaldehyde, and acetic acid.

In any embodiment, the oxygenate comprises one or more alcohols, preferably alcohols having 1 to about 20 carbon atoms, 1 to about 10 carbon atoms, or 1 to about 4 carbon atoms. The alcohols useful as first mixtures may linear or branched, substituted or unsubstituted aliphatic alcohols and their unsaturated counterparts. Non-limiting examples of such alcohols include methanol, ethanol, propanols (e.g., n-propanol, isopropanol), butanols (e.g., n-butanol, sec-butanol, tert-butyl alcohol), pentanols, hexanols, etc and mixtures thereof. In any embodiment described herein, the first mixture may comprise or be one or more of methanol, and/or ethanol, particularly methanol. In any embodiment, the first mixture may be methanol and dimethyl ether.

The oxygenate, particularly where the oxygenate comprises an alcohol (e.g., methanol), may optionally be subjected to dehydration, e.g., catalytic dehydration over e.g., γ-alumina. Typically, such catalytic dehydration decreases the amount of water in the oxygenate by converting a portion of the water and alcohol to an ether, e.g., dimethyl ether (DME) in the first mixture. Further optionally, at least a portion of any methanol and/or water remaining in the first mixture after catalytic dehydration may be separated from the first mixture.

In any embodiment, one or more other compounds may be present in first mixture. Some common or useful such compounds have 1 to about 50 carbon atoms, 1 to about 20 carbon atoms, 1 to about 10 carbon atoms, or 1 to about 4 carbon atoms. Typically, although not necessarily, such compounds can include one or more heteroatoms other than oxygen Some such compounds can include amines, halides, mercaptans, sulfides, or the like, or a combination thereof. Particular such compounds can include alkyl-mercaptans (e.g., methyl mercaptan and ethyl mercaptan), alkyl-sulfides (e.g., methyl sulfide), alkyl-amines (e.g., methyl amine), alkyl-halides (e.g., methyl chloride and ethyl chloride), or a combination thereof. In any embodiment, the amount of such other compounds in the first mixture may be ≤about 2.0 wt %, ≤about 5.0 wt %, ≤about 10.0 wt %, ≤about 15.0 wt %, ≤about 20.0 wt %, ≤about 25.0 wt %, ≤about 30.0 wt %, ≤about 35.0 wt %, ≤about 40.0 wt %, ≤about 45.0 wt %, ≤about 50.0 wt %, ≤about 60.0 wt %, ≤about 75.0 wt %, ≤about 90.0 wt %, or ≤about 95.0 wt %. Additionally or alternatively, the amount of such other compounds in the first mixture may be ≥about 2.0 wt %, ≥about 5.0 wt %, ≥about 10.0 wt %, ≥about 15.0 wt %, ≥about 20.0 wt %, ≥about 25.0 wt %, ≥about 30.0 wt %, ≥about 35.0 wt %, ≥about 40.0 wt %, ≥about 45.0 wt %, ≥about 50.0 wt %, ≥about 60.0 wt %, ≥about 75.0 wt %, or ≥about 90.0 wt %. Ranges expressly disclosed include combinations of any of the above-enumerated upper and lower limits, e.g., 1.0 to 10.0 wt %, 2.0 to 5.0 wt %, 10.0 to 95.0 wt %, wt %, 15.0 to 90.0 wt %, 20.0 to 75.0 wt %, 25.0 to 60 wt %, 30.0 to 50 wt %, 35.0 to 45 wt %, about 40.0 wt %, etc. The oxygenate feed can be derived from any convenient source. For example, the oxygenate feed can be formed by reforming of hydrocarbons in a natural gas feed to form synthesis gas ($H_2$, CO, $CO_2$), and then using the synthesis gas to form alcohols.

In various aspects, the yield of aromatics relative to the total hydrocarbon product can be at least about 53.0 wt %, such as ≥about 55.0 wt %, ≥about 57.0 wt %, or ≥about 59.0 wt %. In some aspects, the total C5+(liquid) product yield can be greater than the yield of aromatics by ≤about 10.0 wt %, such as greater than the yield of aromatics by ≤about 8.0 wt % or by ≤about 6.0 wt %. For example, in an aspect where the yield of aromatics relative to the total hydrocarbon product is about 60.0 wt %, the yield of total liquid product can be about 65.0 wt %. In some aspects, the combined yield of aromatics and olefins in the total hydrocarbon product can be ≥about 70.0 wt %, such as ≥about 75.0 wt % or ≥about 80.0 wt %. It is noted that olefins in the hydrocarbon product can include (gaseous) $C_2$-$C_4$ olefins, and therefore the amount of aromatics plus olefins in the total hydrocarbon product may not necessarily directly relate to the $C_{5+}$ (liquid) yield in the total hydrocarbon product.

In some aspects, converting oxygenates to aromatics and/or olefins in the presence of a catalyst composition as described herein can be beneficial for producing a mixture of aromatics with a desirable composition. For example, in some aspects, converting oxygenates to aromatics as described herein can result in production of aromatics with an increased percentage of $C_9$ and $C_{10}$ aromatics relative to the total aromatics produced. In additional or alternate aspects, production of $C_6$ and $C_7$ aromatics can be enhanced.

In some aspects, converting an oxygenate feed to aromatics in the presence of a catalyst composition as described herein can reduce and/or minimize the amount of coke formation that occurs during conversion.

Suitable and/or effective conditions for exposing the first mixture to a catalyst composition can include temperatures ≥300.0° C., e.g., ≥about 375.0° C., such as ≥about 400.0° C., ≥about 450.0° C., ≥about 460.0° C. Additionally or alternately, the temperature can be ≤about 550.0° C., ≤about 525.0° C., or ≤about 500.0° C. Effective pressures include those wherein the total pressure is ≥1.0 bara, e.g., from 1.0 to about 35 bara. Any suitable oxygenate space velocity may be used. Oxygenate space velocities between about 0.1 h$^{-1}$ to about 20 h$^{-1}$, based on weight of oxygenate relative to weight of catalyst, are typical. In any embodiment, the methods herein can include exposing at least a portion of the first mixture to the catalyst composition at a temperature ≥300° C. and a pressure of 1.0 to about 35 bara, at an oxygenate space velocity of about 0.1 h$^{-1}$ to about 20 h$^{-1}$.

It is noted that the oxygenate feed and/or conversion reaction environment can include water in various proportions. Conversion of oxygenates to aromatics and olefins can result in production of water as a product, so the relative amounts of oxygenate (such as methanol or dimethyl ether) and water can vary within the reaction environment. Based on the temperatures present during methanol conversion, the water in the reaction environment can result in "steaming" of a catalyst. Thus, a catalyst used for conversion of oxygenates to aromatics can advantageously be a catalyst that can substantially retain activity when steamed. Water may additionally or alternately be present in a feed prior to contacting the zeolite catalyst. For example, in commercial processing of methanol to form gasoline, in order to control heat release within a reactor, an initial catalyst stage may be used to convert a portion of the methanol in a feed to dimethyl ether and water prior to contacting a zeolite catalyst for forming gasoline.

Additionally or alternatively, catalysts and methods described herein can be characterized by a deactivation ratio, DR, after processing an amount of oxygenate per gram of the catalyst composition, wherein DR is defined as:

$$DR = \frac{|(A_y - A_{initial})|}{A_{initial}} * 100\%$$

where $A_{initial}$ is defined as the initial selectivity to aromatics (on a weight % of hydrocarbon product basis) at the beginning of oxygenate processing, and $A_y$ is defined as the selectivity to aromatics (on the same basis) after processing "y" grams of oxygenate per gram of catalyst composition. The deactivation ratio, DR, may be ≤about 25.0%, ≤about 20.0%, ≤about 15.0%, ≤about 12.5%, ≤about 10.0%, ≤about 7.5%, ≤about 5.0%, or ≤about 2.5%. Additionally or alternatively, the deactivation ratio, DR, may be ≥2 about 12.5%, ≥about 10.0%, ≥about 7.5%, ≥about 5.0%, ≥about 2.5%, or ≥about 1.0%. Ranges of the deactivation ratio, DR, expressly disclosed include combinations of any of the above-enumerated upper and lower limits, e.g., about 1.0% to about 15.0%, about 2.5 to about 12.5%, about 5.0 to about 10.0%, etc. The deactivation ratio, DR, may be determined after any value of $A_y$ between 200.0 and 400.0, such as 200.0, 250.0, 300.0, 350.0, or 400.0. Combinations of DR and $A_y$ having these upper and lower limits are expressly disclosed, e.g, DR may be 1.0% to about 15.0%, about 2.5 to about 12.5%, about 5.0 to about 10.0%, etc at a $A_y$ of 200.0, 250.0, 300.0, 350.0, or 400.0, such as DR may be ≤about 25.0%, ≤about 20.0%, ≤about 15.0%, or ≤about 10.0% when y=400.0, DR may be ≤about 20%, ≤about 15.0%, ≤about 10.0%, or ≤about 5.0% when y=300.0DR may be ≤about 20%, ≤about 15.0%, ≤about 10.0%, or ≤about 5.0% when y=200.0. Alternatively, DR may be in the range of about 5.0 to about 25.0%, about 5.0 to about 20.0%, about 5.0 to about 15.0, or about 10.0 to about 25.0% when y is 200.0, 300.0, or 400.0.

Additionally or alternatively, embodiments of the invention may be characterized by a resilience of aromatic production after steam treatment at about 540° C. for 24 hours. Resilience refers to the relative amount of aromatics produced by a catalyst composition comprising both a Group 10-12 element and a Group 15 element compared to that produced by a fresh, unsteamed zeolite catalyst composition comprising neither a Group 10-12 nor a Group 15 element. The relative amount of aromatics produced may be ≤about 0.55, ≤about 0.50, ≤about 0.45, ≤about 0.40, ≤about 0.30, ≤about 0.25, or ≤about 0.20. Additionally or alternatively, the relative amount of aromatics produced may be ≤about 0.55, ≤about 0.50, ≤about 0.45, ≤about 0.40, ≤about 0.30, ≤about 0.25, or ≤about 0.20. Ranges of the relative amount of aromatics having these upper and lower limits are expressly disclosed, e.g., about 0.20 to about 0.55, about 0.25 to about 0.50, about 0.30 to about 0.45, about 0.25 to about 0.35, etc.

ADDITIONAL EMBODIMENTS

Embodiment 1

A catalyst composition comprising: a zeolite having a molar ratio of silicon to aluminum of about 10.0 to about 300.0; a Group 10-12 element and combinations thereof; a Group 15 element and combinations thereof; and optionally, a binder, wherein the catalyst composition has a molar ratio of Group 15 element to Group 10-12 element of about 0.01 to about 10.0.

Embodiment 2

A catalyst composition comprising a silicoaluminate zeolite, zinc, phosphorus, and optionally a binder; the zeolite having a molar ratio of silicon to aluminum of about 10.0 to about 300.0, the catalyst composition comprising 0 to about 80.0 wt % binder, based on a total weight of the catalyst composition and having a microporous surface area of ≥about 100.0 m²/g, a molar ratio of zinc to aluminum of about 0.1 to about 1.3, a molar ratio of phosphorus to zinc of 0.01 to 10.0 and at least one of: a) a mesoporous surface area of ≥about 20.0 m²/g, about 20.0 to 500. m²/g, 20.0 to 200.0 or about 30.0 to 100.0 m²/g; and b) a diffusivity for 2,2-dimethylbutane of ≥about $1 \times 10^{-2}$ sec$^{-1}$, $1.25 \times 10^{-2}$ to $3.00 \times 10^{-2}$ sec$^{-1}$, or $1.50 \times 10^{-2}$ to $2.00 \times 10^{-2}$ sec$^{-1}$, when measured at a temperature of about 120° C. and a 2,2-dimethylbutane pressure of about 60 torr (about 8 kPa).

Embodiment 3

The catalyst according to any of Embodiments 1-2, wherein the catalyst composition has a molar ratio of Group 15 element (e.g., phosphorus) to Group 12 element (e.g., zinc) of about 0.2 to about 9.0, about 0.4 to about 8.0, about 0.6 to about 6.0, about 0.8 to about 4.0, about 1.0 to about 3.0, or about 1.5 to about 2.5.

Embodiment 4

The catalyst according to any of Embodiments 1-3, having a Group 12 element (e.g., zinc) to aluminum molar ratio of 0.1 to 1.3, about 0.2 to about 1.2, about 0.3 to about 1.0, or about 0.4 to about 0.8.

Embodiment 5

The catalyst according to any of Embodiments 1-4, wherein the Group 10-12 element is selected from the group consisting of Zn, Cd, and combinations thereof (is zinc).

Embodiment 6

The catalyst according to any of Embodiments 1-5, wherein the zeolite has a molar ratio of silicon to aluminum of about 20.0 to about 200.0, about 30.0 to about 100.0, about 40.0 to about 80.0, about 15.0 to about 100.0 or 20.0 to about 40.0.

Embodiment 7

The catalyst according to any of Embodiments 1-6, wherein the Group 10-12 element (e.g., zinc) is present in an amount of about 0.1 to about 20.0 wt %, about 0.25 to about 10.0 wt %, about 0.5 to about 5.0 wt %, about 0.75 to about 2.0 wt %, or about 1.0 to about 1.5 wt %, based on the total weight of the catalyst composition excluding the weight of any binder if present.

Embodiment 8

The catalyst according to any of Embodiments 1-7, wherein the catalyst composition further comprises at least one Group 2 and/or a Group 3 element, preferably wherein the total weight of the at least one Group 2 and/or Group 3 elements is from about 0.1 to about 20.0 wt %, about 0.25 to about 10.0 wt %, about 0.5 to about 5.0 wt %, about 0.75 to about 2.0 wt %, or about 1.0 to about 1.5 wt %, based on the total weight of the catalyst composition excluding the weight of any binder if present.

Embodiment 9

The catalyst according to any of Embodiments 1-8, wherein the catalyst composition comprises ≤about 80.0 wt %, about 1.0 to about 80.0 wt %, about 5.0 to about 40 wt %, 10.0 to about 35.0 wt %, 10.0 to about 25.0, or about 15.0 to about 20.0 wt %, of the binder, based on a total weight of the catalyst composition.

Embodiment 10

The catalyst according to any of Embodiments 1-9, wherein the catalyst composition has a microporous surface area ≥100.0 m²/g, ≥200.0 m²/g, ≥300.0 m²/g, ≥about 340.0 m²/g, about 340.0 to 1000.0 m²/g, about 350.0 to about 750.0 m²/g, about 360.0 to about 600.0 m²/g, or about 350.0 to about 500.0 m²/g.

Embodiment 11

The catalyst according to any of Embodiments 1-10, wherein the catalyst composition has at least one of the following: (a) a mesoporous surface area of ≥about 20 m²/g, about 20 to 500 m²/g, about 20.0 to 200 m²/g, or about 30 to 100 m²/g; and (b) a diffusivity for 2,2-dimethylbutane of ≥about $1 \times 10^{-2}$ sec$^{-1}$ $1.25 \times 10^{-2}$ to $3.00 \times 10^{-2}$ sec$^{-1}$, or $1.50 \times 10^{-2}$ to $2.00 \times 10^{-2}$ sec$^{-1}$, when measured at a temperature of about 120° C. and a 2,2-dimethylbutane pressure of about 60 torr (about 8 kPa).

Embodiment 12

The catalyst according to any of Embodiments 1-11, wherein the catalyst composition has an alpha value of ≥about 10.0, about 10.0 to about 1000.0, about 10.0 to about 800.0, or about 50.0 to about 700.0.

Embodiment 13

The catalyst according to any of Embodiments 1-12, wherein the catalyst composition comprises a binder having a surface area of ≤about 500.0 m²/g, about 400.0 m²/g, ≤about 200.0 m²/g, about 50.0 to about 200.0 m/g, about 75.0 to about 175.0 m²/g, or about 100.0 to about 150.0 m²/g.

Embodiment 14

The catalyst according to any of Embodiments 1-13, wherein the catalyst composition comprises a binder, and wherein one or more of the following is satisfied: the binder is at least one of substantially free of alumina (i.e., contains about ≤10.0 wt % alumina, ≤about 7.0 wt %, ≤about 5.0 wt %, or ≤about 3.0 wt % alumina) and essentially free of alumina (i.e., contains about ≤1.0 wt %, such as about ≤0.5 wt %, or ≤about 0.1 wt % alumina); and the binder comprises silica, titania, zirconia, cerium oxide, magnesium oxide, or a combination thereof (e.g., is silica).

Embodiment 15

The catalyst according to any of Embodiments 1-14, wherein the catalyst composition comprises from 0 to about 70.0 wt %, particularly, about 5.0 wt % to about 40.0 wt %, binder, based on the total weight of the catalyst composition, and additionally or alternatively has a mesoporosity of about 20 to 500 m²/g.

Embodiment 16

The catalyst according to any of Embodiments 1-15, wherein the catalyst composition has a diffusivity for 2,2-dimethylbutane of $1.25 \times 10^{-2}$ to $3.00 \times 10^{-2}$ sec$^{-1}$, or $1.50 \times 10^{-2}$ to $2.00 \times 10^{-2}$ sec$^{-1}$.

Embodiment 17

The catalyst according to any of Embodiments 1-16, wherein the zeolite satisfies one or more of the following: the zeolite has a constraint index of about 1 to about 12; the zeolite comprises a zeolite having an MFI framework, a zeolite having an MEL framework, a zeolite having a BEA framework, or a combination thereof; the zeolite comprises or is ZSM-5; the zeolite comprises or is ZSM-11.

Embodiment 18

The catalyst according to any of Embodiments 1-17, wherein the catalyst composition has both a) a mesoporous surface area of ≥about 20.0 m$^2$/g, about 20.0 to 500 m$^2$/g, about 20.0 to about 200.0 m$^2$/g, or about 30 to 100 m$^2$/g; and b) a diffusivity for 2,2-dimethylbutane of ≥about 1×10$^{-2}$ sec$^{-1}$, 1.25×10$^{-2}$ to 3.00×10$^{-2}$ sec$^{-1}$, or 1.50×10$^{-2}$ to 2.00× 10$^{-2}$ sec$^{-1}$, when measured at a temperature of about 120° C. and a 2,2-dimethylbutane pressure of about 60 torr (about 8 kPa).

Embodiment 19

The catalyst according to any of Embodiments 1-18, wherein the catalyst composition comprises particles having a size of about 0.01 μm to about 0.6 μm and/or a D$_{90}$ particle size distribution of ≤about 1 μm, ≤about 0.5 μm, or ≤about 0.4 μm.

Embodiment 20

A method for organic compound conversion, comprising: providing a first mixture, the first mixture comprising ≥10.0 wt % oxygenate based on the weight of the first mixture; exposing at a temperature ≥300° C. at a pressure ≥1 bara a catalyst composition of any of Embodiments 1-19 to the first mixture to convert at least a portion of the oxygenate to a hydrocarbons, the hydrocarbons comprising ≥50.0 wt % of aromatics, based on the weight of the hydrocarbons.

Embodiment 21

A method for organic compound conversion, comprising exposing the catalyst composition of any of Embodiments 1-19 to a first mixture comprising ≥10.0 wt % of at least one oxygenate, based on the weight of the first mixture; said exposing being conducted under conditions effective to covert at least a portion of the first mixture into a hydrocarbon containing stream comprising one or more aromatic hydrocarbons.

Embodiment 22

A method for organic compound conversion, comprising exposing the catalyst composition of any of Embodiments 1-19 to a first mixture comprising ≥10.0 wt % of at least one oxygenate, based on the weight of the first mixture; said exposing being conducted under conditions effective to covert at least a portion of the first mixture into a hydrocarbon containing stream comprising one or more aromatic hydrocarbons wherein the hydrocarbon stream comprises ≥50.0 wt % aromatic hydrocarbons.

Embodiment 23

A method for organic compound conversion, comprising exposing the catalyst composition of any of Embodiments 1-19 to a first mixture comprising ≥10.0 wt % of at least one oxygenate, based on the weight of the first mixture; said exposing being conducted under conditions effective to covert at least a portion of the first mixture into a hydrocarbon containing stream comprising one or more aromatic hydrocarbons, the method is characterized by a deactivation ratio, DR, of ≤15 wt % after processing 200.0 to 400 g of oxygenate per gram of the catalyst composition, wherein DR is defined as:

$$DR = \frac{|(A_{200-400} - A_{initial})|}{A_{initial}} * 100\%$$

where A$_{initial}$ is defined as the initial selectivity to aromatics (on a weight % of hydrocarbon product basis) at the beginning of oxygenate processing, and A$_{200-400}$ is defined as the selectivity to aromatics (on the same basis) after processing 200 to 400 grams of oxygenate per gram of catalyst composition.

EXPERIMENTAL

The following examples show data from testing and analysis of a variety of ZSM-5-based self-bound catalyst compositions for performing a methanol to aromatics reaction. After forming ZSM-5 with a desired micropore surface area, the catalysts are formed into self-bound catalyst particles using a procedure similar to the following. It is noted that the absolute values in grams provided below should be considered as representative of using an appropriate ratio of the various components.

ZSM-5 crystal (about 1,400 grams on a solids basis) was added to a mixer and dry mulled. Then, approximately 190 grams of deionized water was added during mulling. After about 10 minutes, about 28 grams of about 50 wt % caustic solution mixed with about 450 grams of deionized water were added to the mixture and mulled for an additional 5 minutes. The mixture was then extruded as formed catalyst pellets. The extrudates were dried overnight at about 250° F. (about 121° C.) and then calcined in nitrogen for about 3 hours at about 1000° F. (about 538° C.). The extrudates were then contacted with a 1N solution of ammonium nitrate, twice. The exchanged extrudates were dried overnight at about 250° F. (about 121° C.) and then calcined in air for about 3 hours at about 1000° F. (about 538° C.).

In the following examples, some of the ZSM-5-based catalyst compositions included a Group 12 element, such as Zn or Cd, and a Group 15 element, particularly phosphorus. To form the catalysts compositions described below, a self-bound catalyst as described above was impregnated via incipient wetness with a solution containing the desired Group 12 and Group 15 elements for impregnation. The impregnated crystal was then dried overnight at about 250° F. (about 12° C.) and then calcined in air for about 3 hours at about 1000° F. (about 538° C.).

In the discussion below, references to the micropore surface area of a catalyst composition correspond to the micropore surface area of the self-bound catalyst. The procedure for self-binding may cause some reduction in micropore surface area of the catalyst composition relative to the micropore surface area of the corresponding zeolite crystals prior to self-binding.

Example 1—Catalyst Composition Versus Aromatics Yield

Figure 1:
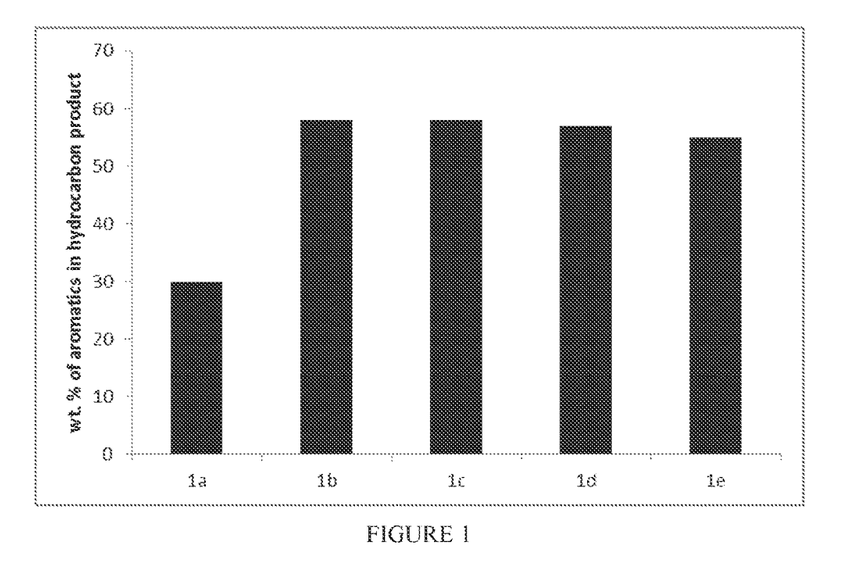
FIG. 1 illustrates the aromatic selectivity of catalyst compositions according to particular embodiments of the invention.

The aromatics yield during methanol conversion of five exemplary ZSM-5 based catalyst compositions (an H-ZSM-5 catalyst, a 1 wt % Zn/H-ZSM-5 catalyst, and three Zn/P/H-ZSM-5 catalysts with various P/Zn ratios (1 wt % Zn in all cases) are shown in Table 1. The aromatic content (wt % of hydrocarbon product) during methanol conversion at about 500° C., an inlet feed pressure of about 15 psig (about 110 kPag), about 20 WHSV (g-CH$_3$OH g-catalyst$^{-1}$ h$^{-1}$), and 100% CH$_3$OH conversion is also shown graphically in FIG. 1. The inlet feed was a mixture of methanol and water, to provide about 13.5 psig (about 95 kPag) of CH$_3$OH and about 1.5 psig (about 11 kPag) of H$_2$O. Unless otherwise indicated, the methanol conversion reactions were performed in a tubular stainless steel reactor. Note that in Table 1 (as well as tables in the other Examples), the ZSM-5 is described in terms of a ratio of Si to Al$_2$. The corresponding molar ratio of silicon to aluminum is half of the value of the Si to Al$_2$ ratio.

For the catalysts in Table 1, all of the catalysts corresponded to self-bound catalysts. As shown in Table 1, the relative increase in aromatic yields afforded by Zn addition to H-ZSM-5 was maintained when P was added to the Zn/H-ZSM-5 catalyst. However, aromatic yields appeared to decrease above a phosphorus loading of about 1 wt %.

TABLE 1

Aromatics Yield as a Function of Catalyst Composition

| Catalyst Composition | Zeolite | Si/Al$_2$ | Zn Content (wt %) | P Content (wt %) | Aromatics (wt %) in hydrocarbon product |
|---|---|---|---|---|---|
| 1a | H-ZSM-5 | ~60 | 0 | 0 | ~30 |
| 1b | H-ZSM-5 | ~60 | 1.0 | 0 | ~58 |
| 1c | H-ZSM-5 | ~60 | 1.0 | 0.3 | ~58 |
| 1d | H-ZSM-5 | ~60 | 1.0 | 0.6 | ~57 |
| 1e | H-ZSM-5 | ~60 | 1.0 | 0.9 | ~55 |

Example 2—Aromatics Yield Versus Amount of Methanol Processed

Figure 2:
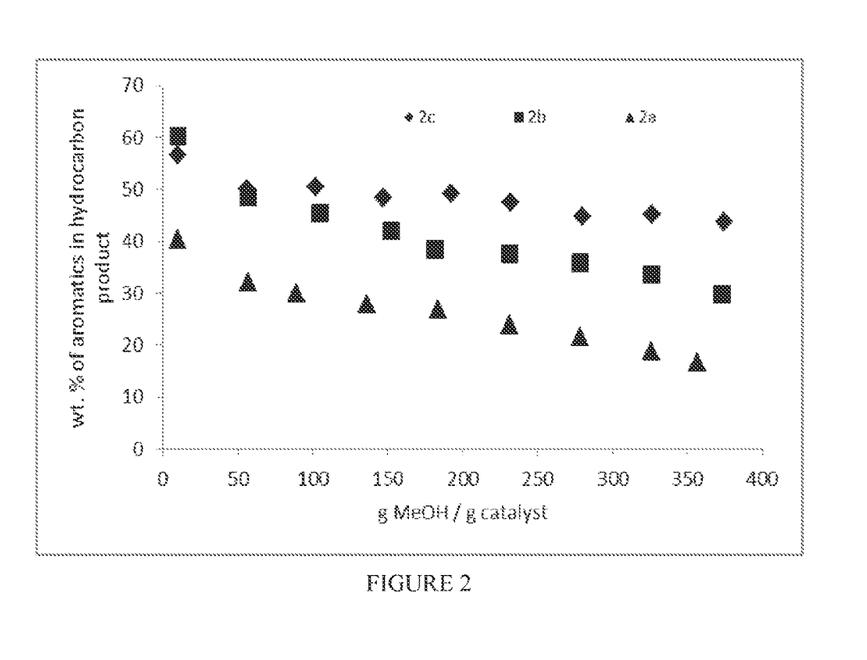
FIG. 2 illustrates the yield of aromatics as a function of methanol processed for catalyst compositions according to particular embodiments of the invention.

In this example, the aromatics yield versus the amount of methanol processed for three exemplary ZSM-5-based catalyst compositions (an H-ZSM-5 catalyst, a 1 wt % Zn/H-ZSM-5 catalyst, and a 1. wt % Zn/1.4 wt % P/H-ZSM-5 catalyst) was determined under substantially the same reaction conditions as in Example 1. Results are tabulated in Table 2. As shown in FIG. 2, the P-containing Zn/H-ZSM-5 catalyst appeared to maintain the highest (45-50%) yield of aromatics with increasing methanol processed (time on stream), whereas the aromatic yields for the H-ZSM-5 and Zn I H-ZSM-5 catalysts appeared to decrease considerably.

TABLE 2

Aromatics Yield versus Amount of Methanol Processed

| Catalyst Composition | Zeolite | Si/Al$_2$ | Zn Content (wt %) | P Content (wt %) | Aromatics Selectivity ($A_{initial}$, wt %) | Aromatics Selectivity ($A_{200}$, wt %) | Aromatics Selectivity ($A_{400}$, wt %) |
|---|---|---|---|---|---|---|---|
| 2a | H-ZSM-5 | ~60 | 0 | 0 | ~40 | ~28 | ~15 |
| 2b | H-ZSM-5 | ~60 | 1.0 | 0 | ~60 | ~40 | ~30 |
| 2c | H-ZSM-5 | ~60 | 1.0 | 1.4 | ~57 | ~50 | ~43 |

Example 3—Effect of Steaming on Aromatic Selectivity

Figure 3:
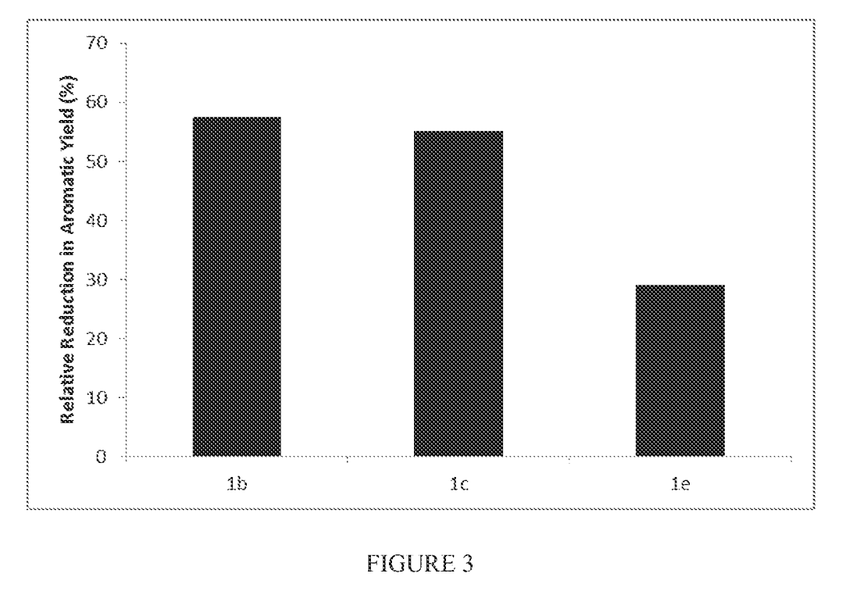
FIG. 3 illustrates the relative reduction in aromatics yield after steam treatment for catalyst compositions according to particular embodiments of the invention.

In this example, the catalyst compositions 1b, 1c, and 1e of Example 1 were steam treated at about 540° C. for 24 hours to simulate an aged catalyst that had undergone severe steam deactivation. Results are reported in Table 3 and illustrated graphically in FIG. 3. These results showed the relative percent reduction in aromatic yields during methanol conversion for the steamed catalyst compositions compared to the fresh, unsteamed Zn/H-ZSM-5 catalyst (i.e., catalyst composition 1a). The relative reduction in aromatic yield for catalyst compositions 1c (0.3 wt % P) and 1e (0.9 wt % P) after steaming appeared to be less than that of the fresh, unsteamed catalyst composition 1a, suggesting that the long term stability of Zn/H-ZSM-5 for aromatic production from methanol may be improved by the addition of phosphorus to the catalyst composition.

TABLE 3

Relative Aromatics Yield After Steam Treatment

| Catalyst Composition | Zn Content (wt %) | P Content (wt %) | Relative Amount of Aromatics in product | Reduction in Aromatic Selectivity (%) |
|---|---|---|---|---|
| 1a | 0 | 0 | 1 | — |
| 1b | 1.0 | 0 | ~0.43 | ~57 |
| 1c | 1.0 | 0.3 | ~0.45 | ~55 |
| 1e | 1.0 | 0.9 | ~0.71 | ~29 |

All documents described herein are incorporated by reference herein for purposes of all jurisdictions where such practice is allowed, including any priority documents and/or testing procedures to the extent they are not inconsistent with this text, provided however that any priority document not named in the initially filed application or filing documents is NOT incorporated by reference herein. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law. Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

What is claimed is:

1. A catalyst composition comprising:
   a zeolite comprising ZSM-5, ZSM-11, a zeolite having an MFI framework, a zeolite having an MEL framework, a zeolite having a BEA framework, or a combination thereof having a molar ratio of silicon to aluminum of about 10.0 to about 300.0;
   a Group 10-12 element and combinations thereof;
   phosphorus is present in an amount of ≤about 1.0 wt %; and
   optionally, a binder,
   wherein the catalyst composition has a molar ratio of phosphorus to a Group 10-12 element of about 0.01 to about 10.0.

2. The catalyst composition of claim 1, wherein the catalyst composition has a molar ratio of phosphorus to Group 10-12 element of about 0.2 to about 9.0.

3. The catalyst composition of claim 1 having a Group 10-12 element to aluminum molar ratio of 0.1 to 1.3.

4. The catalyst composition of claim 1, wherein the Group 10-12 element is selected from the group consisting of Zn, Cd, and combinations thereof.

5. The catalyst composition of claim 1, wherein the Group 10-12 element is zinc.

6. The catalyst composition of claim 1, wherein the zeolite has a molar ratio of silicon to aluminum of about 20 to about 200.

7. The catalyst composition of claim 1, wherein the Group 10-12 element is present in an amount of about 0.1 to about 20.0 wt, based on the total weight of the catalyst composition excluding the weight of any binder.

8. The catalyst composition of claim 1, further comprising at least one Group 2 and/or a Group 3 element.

9. The catalyst composition of claim 1 having a microporous surface area of about 100.0 to 1000.0 $m^2/g$.

10. The catalyst composition of claim 1 having at least one of the following:
    (a) a mesoporous surface area of about 20 to 500 $m^2/g$; and
    (b) a diffusivity for 2,2-dimethylbutane of $1.25 \times 10^{-2}$ to $3.00 \times 10^{-2}$ $sec^{-1}$, when measured at a temperature of about 120° C. and a 2,2-dimethylbutane pressure of about 60 torr (about 8 kPa).

11. The catalyst composition of claim 1, wherein the catalyst composition has an Alpha value of about 1.0 to about 1000.0.

12. The catalyst composition of claim 1, wherein the binder has a surface area of ≤about 500 $m^2/g$.

13. The catalyst composition of claim 1, wherein the catalyst composition comprises from about 0 wt % to about 70.0 wt % binder, based on the total weight of the catalyst composition and has a mesoporosity of about 0.30 to about 1.0 $cm^3/g$.

14. The catalyst composition of claim 1, wherein the catalyst composition has a diffusivity for 2,2-dimethylbutane of $1.25 \times 10^{-2}$ to $3.00 \times 10^{-2}$ $sec^{-1}$.

15. The catalyst composition of claim 1, wherein the zeolite has a constraint index of about 1 to about 12.

16. The catalyst composition of claim 1, wherein the zeolite is ZSM-5.

17. The catalyst composition of claim 1, wherein the zeolite is ZSM-11.

* * * * *